United States Patent
Ishiguro

(10) Patent No.: US 6,509,966 B2
(45) Date of Patent: Jan. 21, 2003

(54) OPTICAL SYSTEM FOR DETECTING SURFACE DEFECT AND SURFACE DEFECT TESTER USING THE SAME

(75) Inventor: Takayuki Ishiguro, Tokyo (JP)

(73) Assignee: Hitachi Electronics Engineering Co., Ltd., Tokyo (JP)

(*) Notice: Subject to any disclaimer, the term of this patent is extended or adjusted under 35 U.S.C. 154(b) by 0 days.

(21) Appl. No.: 09/907,713

(22) Filed: Jul. 19, 2001

(65) Prior Publication Data

US 2002/0080345 A1 Jun. 27, 2002

(30) Foreign Application Priority Data

Dec. 27, 2000 (JP) ........................... 2000-397091

(51) Int. Cl.[7] ............................................. G01N 21/00
(52) U.S. Cl. ..................................................... 356/237.2
(58) Field of Search ....................................... 356/237.2

(56) References Cited

U.S. PATENT DOCUMENTS 5,898,491 A * 4/1999 Ishiguro et al. ........... 356/237.2

FOREIGN PATENT DOCUMENTS

JP     10-325713    12/1998

* cited by examiner

Primary Examiner—Harold I. Pitts
(74) Attorney, Agent, or Firm—Mattingly, Stanger & Malur, P.C.

(57) ABSTRACT

A defect detection optical system includes a light receiving system including n light receiving elements arranged in a direction perpendicular to a main scan direction, for focusing an image thereon such that the image becomes in the arranging direction of the light receiving elements, in which, when a width of the image focused thereon in the main scan direction is equal to or smaller than the width of the light receiving elements, light reflected from a recessed or protruded defect is swung in the width direction of the light receiving elements and a light receiving area of the light receiving elements is reduced. When the reflection light from the recessed or protruded defect is; swung in sloped portions of the defect, an amount of light received by the light receiving elements is at least reduced, so that two detection signals having levels lower than those when there is no defect are obtained.

12 Claims, 4 Drawing Sheets

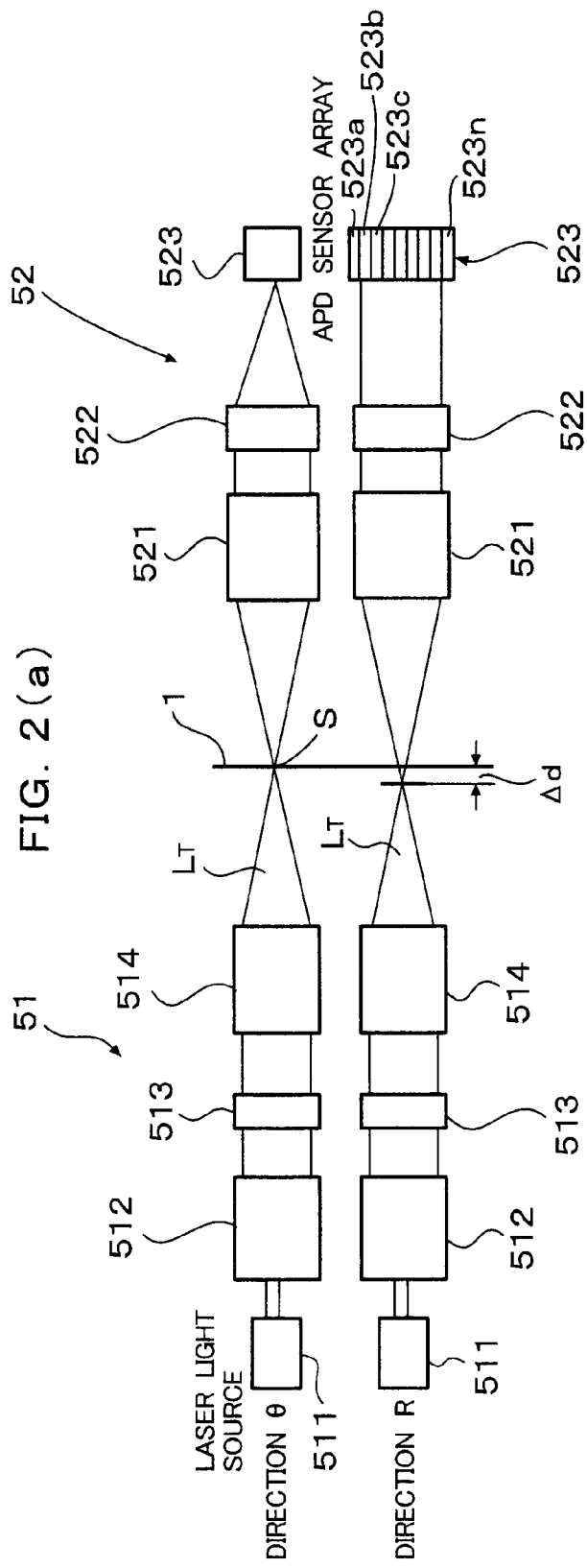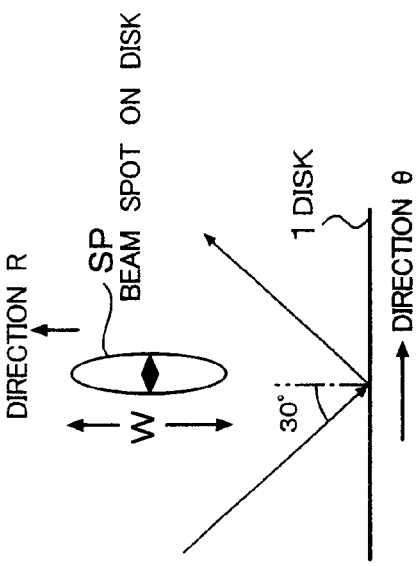

OPTICAL SYSTEM FOR DETECTING SURFACE DEFECT AND SURFACE DEFECT TESTER USING THE SAME

BACKGROUND OF THE INVENTION

1. Field of the Invention

The present invention relates to an optical system for defecting a surface defect and a surface defect tester and, particularly, the present invention relates to an optical system for use in a detection of surface defect of a flat plate such as a magnetic disk or a glass substrate thereof to detect the size of irregularity of a surface of the flat plate with high precision and the surface defect tester using the same optical system.

2. Description of the Prior Art

A magnetic hard disk used as a recording medium of a computer system is tested for surface defect and size of the surface defect in a substrate state or in a complete magnetic disk state in which a magnetic film is painted thereon.

The size of the recent magnetic disk is 3.3 inches or smaller and the recording density thereof is substantially increased by the employment of a giant magneto-resistance (GMR) head. In such magnetic disk, a glass substrate, which has thermal expansion coefficient smaller than that of the conventional aluminum substrate and is as thin as in a range from 0.6 mm to 0.8 mm, is used.

FIG. 5($a$) shows a main construction of a conventional surface defect tester 10 for magnetic disk.

The surface defect tester 10 shown in FIG. 5($a$) is constructed with a rotary mechanism 2, a detection optical system 3 and a surface defect detection/processor 4. A disk 1 to be tested is mounted on a spindle 21 of the rotary mechanism 2 and rotated by a motor (M) 22. On the other hand, the detection optical system 3 is constructed with a light illuminating system 31 including a laser light source 311 and a condenser lens 312 and an optical light receiving system 32 including a condenser lens 321 and a light receiver 322. A laser beam $L_T$ produced by the laser light source 311 is condensed by the condenser lens 312 to a laser spot Sp on a surface of the disk 1.

When the disk 1 is moved horizontally while being rotated, the laser spot Sp moves in a radial direction R of the disk 1, so that a surface of the disk 1 is scanned spirally. In this case, in order to make a total scan time of the disk 1 as short as possible, an area of the laser spot Sp is made ellipsoidal having a length $\phi_1$ in a minor axis direction and a length $\phi_2$ in a major axis direction as shown in FIG. 5($b$) and the major axis is set perpendicular to the scan direction to increase a scan width of the laser spot. The laser spot Sp is scattered by a defect F of the surface of the disk. A reflected light SR is condensed by the condenser lens 321 of the optical light receiving system 32 and the condensed light is received by the light receiver 322 including the optoelectric converter element such as, for example, an avalanche photodiode (APD) or a photo multiplier tube (PMT). An output signal of the light receiver 322 is inputted to a signal processing circuit 41 of the surface defect detection/ processing unit 4. The defect F is detected by a defect detection signal output from the signal processing circuit 41. The size of the defect F is detected or calculated according to a level of the detection signal outputted from the light receiver 322. The signal processing circuit 41 for detecting the defect and classifying or calculating the size of detected defects by the so-called sampling includes an amplifier for amplifying the output signal of the light receiver 322, a sampling circuit for sampling peak values of the amplified output signal, which corresponds to a defect and is larger than noise component of the output signal with a pulse supplied from a rotary encoder 23 to detect the peak values of the sampled output signal, an A/D converter for digitizing the sampled peak value and a position data producing circuit responsive to the pulse signal from the rotary encoder 23 for producing a position data on the disk, etc.

The size data of the respective defects and the position data of the detects on the disk are converted into digital data by the signal processing circuit 41 and inputted to the data processor 44 composed of an MPU 42 and a memory 43, etc. The number of defects of each size are counted by the data processor 44 and the size data and the count value of the defects, etc., are outputted to a printer (PR) 45 together with the position data of the defects on the disk 1. In this case, these data may be printed out as a map on the disk. Alternatively, the defect size is displayed on a display (CRT) 46, etc., together with the position thereof on the disk and the count value of the defects is displayed separately.

Incidentally, the rotary encoder 23 is provided in the vicinity of a rotary shaft of the motor 22 or in engagement therewith, detects an amount of rotation of the disk with reference to a reference position provided on the disk and sends a pulse signal corresponding to the amount of rotation of the disk to the signal processing circuit 41.

In order to clearly detect the size of recessed defect and protruded defect, the surface defect tester 10 optimally sets factors related to the detection sensitivity, such as illumination angle $\theta_T$ of the laser beam $L_T$ of the optical illuminating system 31, light receiving angle $\theta_R$ of the light receiving system 32, voltage V applied to the light receiver (APD) 322 or gain of the amplifier provided in the signal processing circuit 41, threshold voltage E for removing noise and laser output of the laser light source 311, etc., through the control panel 47. Incidentally, the detection sensitivity is regulated by using, as a sample disk, a practical disk having recessed defects such as dish-like defect, pit-like defect or scratch: defect having known size or a practical disk having protruded defects having a specific height.

JP H10-325713A assigned to the assignee of this application and belonging to the same technical field as that of the above mentioned prior art discloses a technique titled "Surface Defect Test Method and Surface Defect Tester", in which a defect test is performed by using a sensitivity calibration disk having a plurality of radially extending dummy defect rows each including a plurality of protruded or recessed defects whose sizes are changed in steps: and the detection sensitivity is regulated correspondingly to the dummy defect row including defects whose sizes are increased or decreased in steps, by displaying the dummy defect row as a result of the test.

However, in such conventional defect detection system for disk in which a recessed defect of a disk or a protruded defect including extraordinary substance, etc., on the disk is detected by comparing a level of reflected or scattered light detected by a light receiver with a reference level, the size of the defect is detected as a level of received light, so that the detected defect size becomes inaccurate. Particularly, for the recessed defect or the protruded defect, depth or height of the defect influences the level of received light, so that the detection accuracy of defect size, which is an area extended in a flat plane, is low.

The sensitivity calibration disk used in this tester corresponds to U.S. Pat. No. 5,975,027, the content of which is shown in FIGS. 5($a$) and 5($b$).

Recently, it is required to improve the preciseness of defect configuration measurement and the preciseness of defect classification. However, it is impossible to precisely perform the classification of defects by the above mentioned prior art.

In order to solve this problem, JP H11-358769A assigned to the assignee of the present application discloses a technique in which a sensor arrangement including a plurality of APD elements is used as the light receiver 322 and a zigzagged stripe pattern corresponding to the APD elements is provided in front of the sensor arrangement. The recessed defect and the protruded defect are detected on the basis of a difference in amount of received light between adjacent APD elements of the sensor arrangement.

However, this technique requires the zigzagged stripe pattern and a number of detection circuits are necessary to detect the differences in light amount between adjacent sensor elements.

SUMMARY OF THE INVENTION

An object of the present invention is to provide a defect detecting optical system capable of precisely detecting the size of recessed or protruded defect on a surface of a flat plate and a surface defect detector using the same defect detecting optical system.

Another object of the present invention is to provide a surface defect detector capable of precisely detecting the depth or height of recessed or protruded defect on a surface of a flat plate and capable of easily classifying defects.

In order to achieve the above objects, a defect detecting optical system and a surface defect detector according to the present invention is featured by comprising a light illuminating system for emitting light beam having a width in a direction perpendicular to a main scan direction to relatively scan a surface of a flat plate and a light receiving system having a light receiver including a plurality (n) of light receiving elements arranged in the direction perpendicular to the main scan direction for picking up an image of a portion of the flat plate at a scan position, wherein, when a width of the image in the main scan direction is equal to or smaller than the width of the light receiving element and a certain one of the light receiving elements receives light reflected from the recessed or protruded defect, the reflected light is swung in the width direction of the certain light receiving element, which is perpendicular to the arranging direction of the light receiving elements, so that an amount of light received by the certain light receiving element is at least reduced.

With this construction of the defect detection optical system, which comprises the light illuminating system for emitting light beam having width in the direction perpendicular to the main scan direction to relatively scan the surface of the flat plate and the light receiving system including the n light receiving elements arranged in the direction perpendicular to the main scan direction for picking up an image of the flat plate at a scan position and in which, when the width of the image in the main scan direction is equal to or smaller than the width of the light receiving element and the certain one of the light receiving elements receives light reflected from the recessed or protruded defect, the reflected light is swung in the width direction of the certain light receiving element causing the amount of light received by the certain light receiving element to be at least reduced, it is possible to obtain a detection signal having magnitude, which is large when there is no defect on the surface of the flat plate and small when there is a defect thereon.

Since it is usual that there are a pair of slanted side faces in the recessed or protruded defect in the main scan direction, two detection signals are obtained for one defect. Therefore, it is possible to easily detect the size of the defect at that position on the basis of a distance between the two detection signals. Particularly, when n light receiving elements are arranged in a radial direction R, a plurality of light receiving elements arranged to cover an area of an image of a defect in the radial direction can detect the defect simultaneously. Consequently, it is possible to easily calculate the area of the defect.

Further, it is possible to easily determine the continuity of defect on the basis of a relation between defect detection coordinates assigned to the n light receiving elements determined correspondingly to the scan, respectively, and the detection signals from the respective light receiving elements. According to the continuity determination, it is possible to calculate an area of a defect among the recessed and protruded defects, which is somewhat deformed. Further, it is possible to precisely detect the depth of recessed defect or the height of protruded defect by averaging the levels of the two detection signals.

As a result, it is possible to realize the defect detecting optical system, which is capable of precisely detecting the size of the recessed and/or protruded defect on the surface of the flat plate and, further, precisely detecting the size and depth or the size and height of the recessed or protruded defect on the surface of the flat plate, and to realize the surface defect tester, which is capable of easily classifying defects.

BRIEF DESCRIPTION OF THE DRAWINGS

FIG. 2(a) and FIG. 2(b) illustrate a light emitting/light receiving system of a detecting optical system, extended in a direction (θ) in parallel to the drawing sheet and in a direction (R) perpendicular to the drawing sheet;

DETAILED DESCRIPTION OF THE PREFERRED EMBODIMENTS

Figure 1:
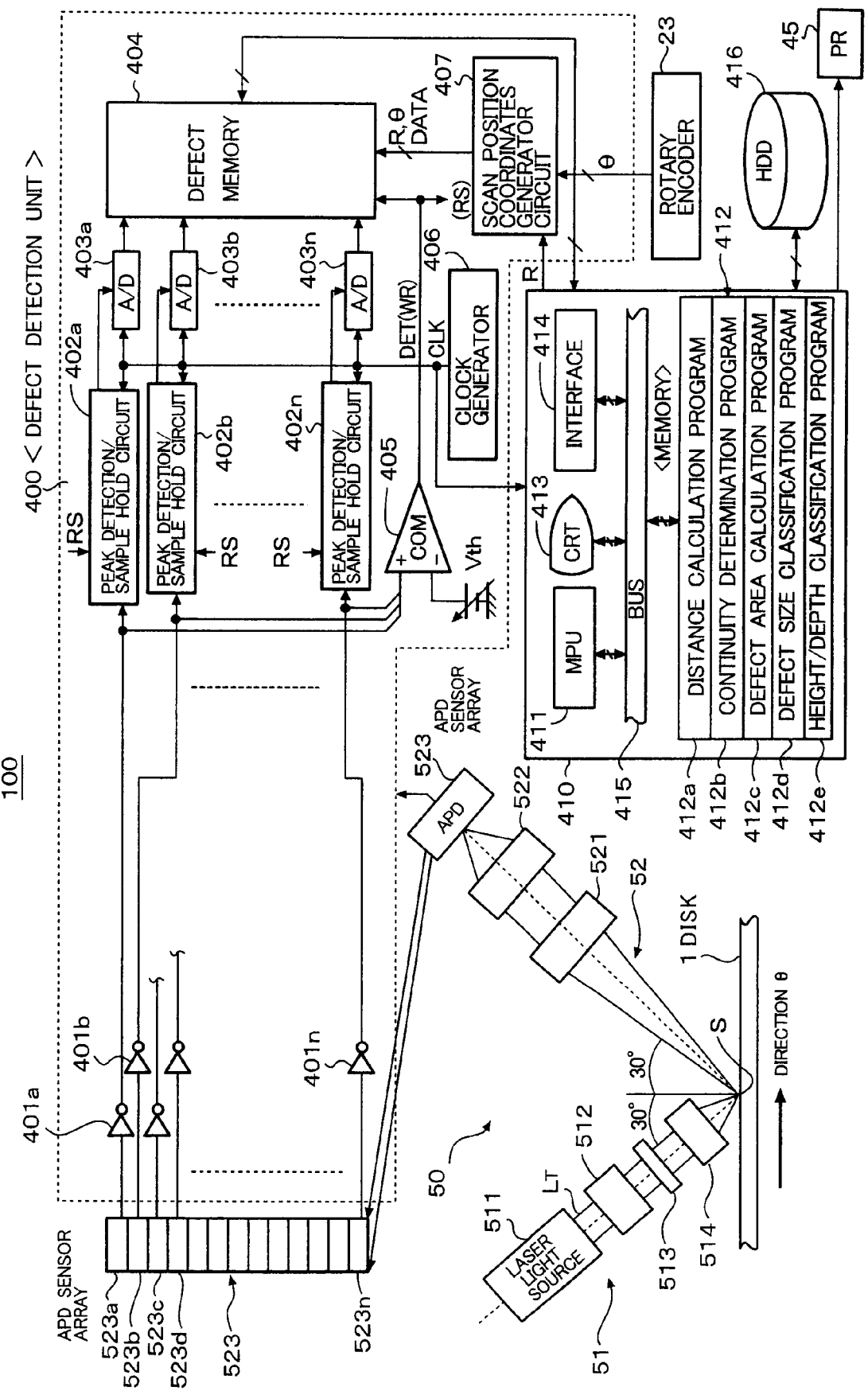
FIG. 1 is a block circuit diagram of an embodiment of a surface defect tester to which the present invention is applied.

In FIG. 1, a surface defect tester 100 includes a detecting optical system 50 and a defect detecting portion 400. The detecting optical system 50 includes a light emitting system 51 and a light receiving system 52. The light emitting system 51 includes a laser light source 511 for emitting a laser beam $L_T$, a laser beam expander 512 for expanding the laser beam $L_T$ in a direction (R) perpendicular to the drawing sheet, a cylindrical lens 513 and a focusing lens 514. The laser beam $L_T$ expanded by the laser beam expander 512 is focused on a surface of a disk 1 while a focus point of the laser beam $L_T$ is shifted in the side of the beam expander in the radial direction R by an offset Δd from the beam waist, which is a point corresponding to a laser wave source through the cylindrical lens 513 and the focusing lens 514, as shown in FIG. 2(a). Therefore, the beam spot Sp is expanded to have an ellipsoidal cross section having width W in a major axis thereof as shown in FIG. 2(b).

In FIG. 1, in a disk rotating direction, that is, direction θ parallel to the drawing sheet, light beam passed through the cylindrical lens 513 is focused on a test point S on the disk 1 as a point spot by the focusing lens 514 as shown by a symbol ♦ in FIG. 2(b). In the direction θ, a illumination angle thereof is about 30° with respect to a normal line to the disk 1, as shown in FIG. 2(b). The cross section of the beam spot at the test point S of the disk in the direction R perpendicular to the drawing sheet becomes ellipsoidal having the constant width W (for example, about 150 μm to about 200 μm) large enough to cover an arrangement area, of light receiving elements in the image plane. This is a difference from the beam spot Sp shown in FIG. 5.

Figure 3:
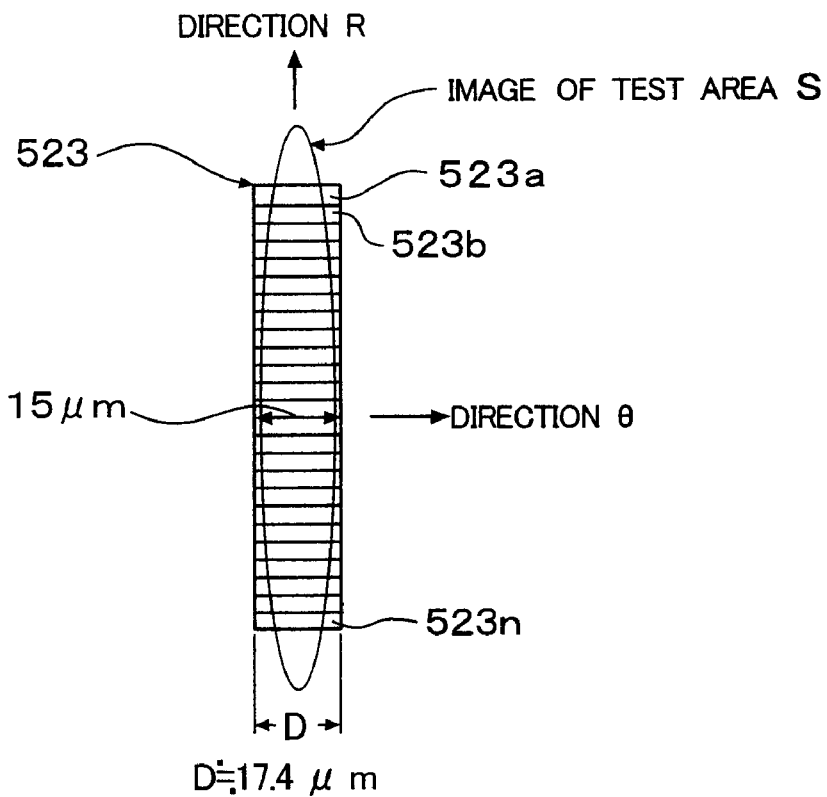
FIG. 3 shows a relation between an image focused on a light receiving plane of a test area and an APD sensor array.

The light receiving system 52 includes an objective lens 521 and receives a light mirror-reflected from the test point S of the disk 1 through the objective lens 521. The mirror-reflected light is converted into parallel light by the light receiving system 52 and guided to a focusing lens 522 to focus an image of the test point S on a light receiving plane of an APD sensor array 523. As shown in FIG. 3, the APD sensor array 523 includes a plurality (n) of light receiving elements arranged along the image in a radial direction R (direction perpendicular to the drawing sheet in FIG. 1) of the disk 1, where n is an integer larger than 1. The number of the light receiving elements may be, for example, 23. The image of the test point S is focused on the APD sensor array 523 such that the width W of the image of the test point S, which is about 150 μm to about 200 μm, covers the APD sensor array 523, which is about 120 μm long. Width of each APD sensor is 0.5 mm, which corresponds to about 5 μm on the surface of the disk 1.

FIG. 2(a) illustrates a light emitting/light receiving system of a detecting optical system, extended in a direction θ parallel to the drawing sheet and in a direction R perpendicular to the drawing sheet.

As shown in a lower portion of FIG. 2(a), in the direction θ, the laser beam $L_T$ from the laser light source 511 is expanded by the beam expander 512 and condensed on the test point S as a spot (the symbol ♦ shown in FIG. 2(b)) by the focusing lens 514 having a focal point on the surface of the disk 1. Light mirror-reflected from the test point S is received by the light receiving elements of the APD sensor array 523 through the objective lens 521 and the focusing lens 522.

On the other hand, in the radial direction R, the laser beam $L_T$ from the laser light source 511 is expanded by the beam expander 512 and condensed on the test point S by the focusing lens 514 having a focal point shifted to a position on the side of the focusing lens 514, which is remote from the surface of the disk 1 by an offset amount of Δd (see FIG. 2(b)). Light mirror-reflected from the test point S is received by the light receiving elements 523a, 523b, 523c, ~523n of the APD sensor array 523, which are arranged in the width direction of the APD sensor array, through the objective lens 521 and the focusing lens 522.

Figure 5A:
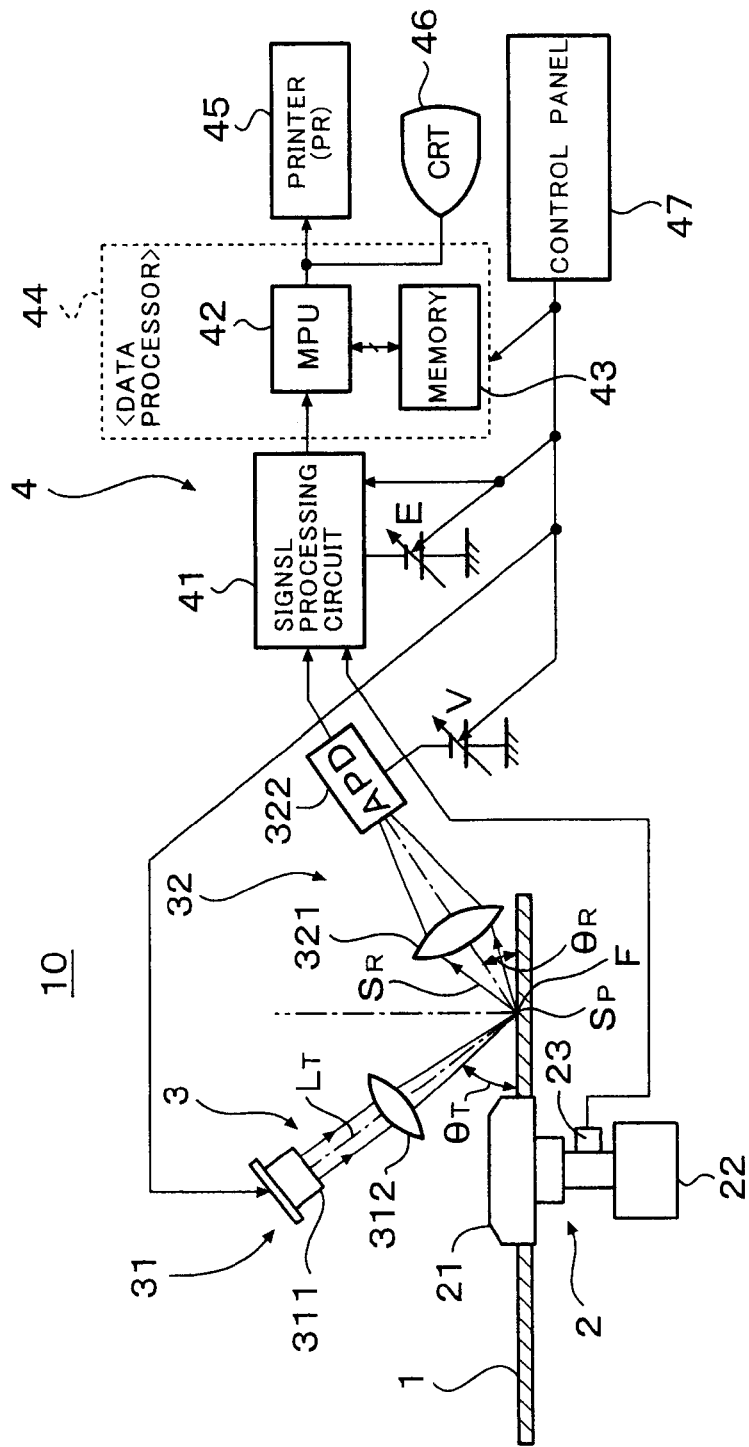
FIG. 5(a) is a block circuit diagram of a main portion of the surface defect tester for a magnetic disk surface.
Figure 5B:
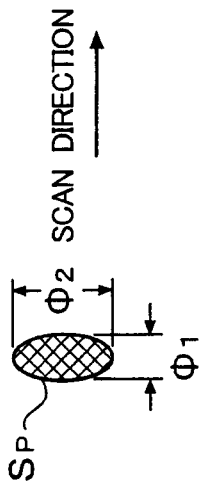
FIG. 5(b) illustrates a cross sectional configuration of a light beam focused on a test point.

As shown in FIG. 1, detection signals obtained from the n light receiving elements 523a~523n of the APD sensor array 523, which are arranged in the direction R, are inputted to the defect detection unit 400 corresponding to the signal processing circuit 41 of the surface defect detecting processor 4 shown in FIG. 5. Data of a defect F and the depth or height of the defect F are produced by the defect detection unit 400. These defect data are inputted to a data processor 410 composed of an MPU 411 and a memory 412, etc. In the data processor 410, an area of the defect F is calculated and the size of the defect F is classified according to the calculated area thereof and the depth or height thereof. The size classification of the defect F is printed out by a printer 45 together with a position of the defect on the disk 1. The classification is also displayed on a display 413 such as CRT together with the position on the disk and the number of defects in the same class is displayed separately from the display of the size classification.

The image of the test area S is focused on the n light receiving elements 523a~523n arranged in the direction R, such that the image is limited within the light receiving areas of the light receiving elements, as shown in FIG. 3. That is, a width of the image of the test area S is equal to or smaller than the width D of the light receiving element when there is no defect detected. Therefore, when there is no defect detected, the level of the detection signal outputted from each light receiving element of the APD sensor array 523 becomes maximum. When a defect is detected, the image of the test area S is swung leftward or rightward in FIG. 3, so that the level of the detection signal of each light receiving element is lowered correspondingly to an amount of swing of the image. When the image off the test area S becomes out of the light receiving area of the light receiving element, the level of the detection signal becomes substantially zero.

Figure 4A:
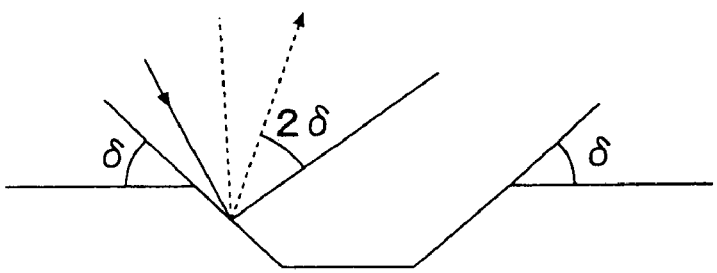
FIG. 4(a) illustrates light reflection from a recessed defect.

FIG. 4(a) shows a case where light mirror-reflected by a recessed or protruded defect is swung left or right.

When the laser light $L_T$ scanning the disk 1 in the direction θ reaches a recessed defect on the disk, the mirror-reflected light is rotated clockwise direction by 2δ as shown in FIG. 4(a), where δ is an angle of a front side slope of the recessed defect with respect to the surface of the disk. Therefore, the mirror-reflected light from the test point S in the direction θ is deviated by 2δ. With this deviation of reflected light, the image on the light receiving element receiving mirror-reflected light corresponding to the recessed defect shown in FIG. 3 is moved rightward from a center position. Thereafter, a bottom of the defect is scanned, so that the image on the light receiving element is returned to the center position. On the contrary, when the laser beam $L_T$ goes beyond a rear side slope of the defect, the light mirror-reflected by the rear slope slanted by δ in an opposite direction is moved leftward from the center position of the light receiving element and, thereafter, returned to the center position.

On the other hand, in a case of a protruded defect, a front and rear slopes thereof become opposite to the front and rear slopes of the recessed defect, respectively. Therefore, the image on the light receiving element is moved leftward from the center position first and then returned to the center position and, thereafter, moved rightward from the center position and returned to the center position.

Further, in a case where a defect is deep or a high, the amount of leftward as well as rightward deviation of mirror-reflected light on the light receiving element becomes large and, when the defect becomes deeper or higher, the image on the light receiving element is moved completely out of the light receiving area thereof and, then, returned to the center position.

Figure 4B:
FIG. 4(b) illustrates a detected waveform obtained by the light reflection.

As a result, a detection signal such as shown in FIG. 4(b) is obtained correspondingly to the depth or height of the recessed or protruded defect and the level thereof is substantial when the depth or height is large.

Returning to FIG. 1, the detection signals from the light receiving elements 523a to 523n are inverted and amplified by inversion amplifiers 401a to 401n provided correspondingly to the respective light receiving elements to obtain positive peak signals. The positive peak signals are inputted to peak detection/sample hold circuits 402a to 402n, respectively. Peak values of two peaks of the detection signal (obtained by inverting the signal shown in FIG. 4(b)) are detected for each of the light receiving elements. The detected peak values are digitized by A/D converters 403a to 403n, respectively, and stored in a defect memory 404.

The peak detection/sample hold circuits 402a to 402n receive a clock signal CLK from a clock generator 406 and hold the peak values as sample values correspondingly to the clock CLK.

Outputs of the inversion amplifiers 401a to 401n are inputted to a defect detection circuit 405. The defect detection circuit 405 includes a hysterisis comparator. The hysterisis comparator compares the outputs of the inversion amplifiers 401a to 401n with a predetermined value Vth under OR condition and generates a defect detection signal DET when the output level of any one of the inversion amplifiers rises beyond the predetermined value. The generation of the defect detection signal DET is stopped when the output level of the inversion amplifier falls below the predetermined value corresponding to a value in the vicinity of the peak value. The falling value (rear edge) of the output of the inversion amplifier at the time when the generation of the defect detection signal DET is stopped is sent to the defect memory 404 as a write control signal WR. The write control signal WR is slightly delayed and inputted to the respective peak detection/sample hold circuits 402a to 402n as a reset signal RS for resetting preceding values held therein.

As a result, the peak values in a period from the generation of the defect detection signal DET to the stoppage of the defect detection signal DET are sent from the A/D converters 403a to 403n to the defect memory 404 and stored therein as the defect data. The level at this time represents the depth of recessed defect or the height of protruded defect. Further, a distance between peak values corresponds to the size of defect.

Such defect data is stored in updated addresses of the defect memory 404 together with the position data of in the directions R and θ. This address is updated every write of the defect data. The positional coordinates data of R and θ are generated by a scan position coordinates generator circuit 407.

The write control signal WR may be generated by the peak detection/sample hold circuits 402 with a timing of not the falling of the defect detection signal DET but the detection of peak.

The scan position coordinates generator circuit 407 receives an index signal indicative of a rotational reference position of the disk 1 and a rotation angle signal θ of the disk 1 from a rotary encoder 23 and the coordinates of a current position of the disk in the radial direction R from the data processor 410 to generate the scan position coordinates in the directions R and θ and sends the data to the defect memory 404 as the position data.

As a result, the defect memory 404 stores the level of the detection signal corresponding to the depth or height of the defect and the positions in which the two detection signals for one recessed or protruded defect are generated every time when the defect is detected.

The clock generator circuit 406 supplies the clock signal CLK to the A/D converters 403a to 403n, the peak detection/sample hold circuits 402a to 402n and the data processor 410, etc.

The calculation of the area of defect and the classification of the size of defect, which are performed by the data processor 410, will be described.

In FIG. 1, the data processor 410 is constructed with an MPU 411, a memory 412, a CRT display 413 and an interface 414, etc., which are mutually connected through a bus 415. The defect data obtained from the defect memory 404 are stored in the memory 412 through the interface 414 and the bus 415 under control of the MPU 411 at a time when a spiral scan of the disk 1 is completed.

The memory 412 stores a distance calculation program 412a for calculating a distance between the detection signals, a continuity determination program 412b, a defect area calculation program 412c, a defect size classification program 412d and a height/depth classification program 412e, etc. Various data files for size classification are stored in an external memory 416 such as HDD (hard disk drive) connected to the data processor 410 through the interface 414.

The distance calculation program 412a is executed by the MPU 411. The MPU 411 reads the defect data stored in the defect memory 404 in the memory 412, calculates a distance L between adjacent two peak values of the defect data, which corresponds to the length of the defect, on the basis of the detected coordinates thereof and, when the distance L is smaller than the reference value S, determines the data as originated from one defect. Further, the MPU 411 calculates a coordinates of a center position between the two peaks on the basis of the detected coordinates values of the two peaks and stores the calculated distance L corresponding to the length of defect and the coordinates of the center position sequentially. Thereafter, the MPU 411 performs a similar processing for adjacent peak values of a next defect data and calls the continuity determination program 412b at a time when the above processing is completed. When the distance L between adjacent peak values of one defect is larger than a reference value S, the MPU 411 stores in the memory 412 the distance as being zero and the coordinates of the defect data as the center coordinates of the defect.

The continuity determination program 412b is executed by the MPU 411. At a time when the distances L of all of the defect data are calculated, the MPU 411 determines a continuity of defect data of adjacent defects by determining, on the basis of the center coordinates, the distances L and the detection width (about 5 μm in this embodiment) of each light receiving element, whether or not about 5 μm wide portions of the distances L are overlapped both vertically and horizontally. Defect data, which are continuous, are grouped as one defect data. The grouped defect data of defects detected from an innermost or outermost periphery of the disk are numbered sequentially and stored in the memory 412. Thereafter, the MPU 411 calls the defect area calculation program 412c.

Incidentally, since the defect detection is performed for one defect or a plurality of defects in the direction θ by the light receiving elements arranged in the direction R correspondingly to the size of defect, the determination of continuity of defect becomes possible when the detection coordinates of the defects in the direction θ are within the length L of defect and the coordinates thereof in the direction R are adjacent each other. It may be possible to determine the continuity of defect by tracing, along the direction R, the defects within the length L and having same coordinates in the direction θ. In the latter case, the determination of defect continuity becomes easier.

Since, in this embodiment, the defect is detected by the n light receiving elements, the detected coordinates of the defect in the direction R can be determined by fractionating the coordinates of the defect detection positions in the direction R, which are stored in the defect detection memory 404, correspondingly to the positions of the n light receiving elements. In this case, the preciseness of the detection coordinates in the direction R is made n times by adding the detection positions of the n light receiving elements as the detection coordinates in the direction R. With this construction, it is possible to improve the resolution of defect detection in the direction R. When a plurality of adjacent light receiving elements among the n light receiving elements detect one defect in the direction R, the coordinates of the light receiving element located in a center of the plurality of light receiving elements is used as the detection coordinates of the defect in the direction R.

The defect area calculation program 412c is executed by the MPU 411. By executing this program, the MPU 411 calculates an area of a grouped one defect. As to a defect, which has only one peak, the defect is decided as an independent defect having an area of 5 μm and having no continuity in the direction R and an area of the defect is calculated by length L×5 μm. Thereafter, the MPU 411 calls the defect size classification program 412d.

The defect size classification program 412d is executed by the MPU 411. By executing this program, the MPU 411 classifies the areas of defects calculated as mentioned above to 5 classes, very large, large, middle, small and very small, according to classification references and stores a result of classification together with defect numbers. Thereafter, the MPU 411 calls the height/depth classification program 412e.

The height/depth classification program 412e is executed by the MPU 411. By executing this, the MPU 411 calculates an average of the values of the defect data in the defect memory 404, which are stored in the memory 412 in the order of the defect numbers, that is, absolute values of peak values of the detection signal obtained from one of the defect groups, classifies the defect for size by using the average value as the height or depth of the defect and stores the size of the defect in the memory 412 together with the defect number thereof. When one defect does not include a plurality of defect data, such average value is not used. Since it is usual that a defect data of one recessed or protruded defect includes two or more peak values, the depth or height of each defect can be calculated by the average value, so that the preciseness of detection is improved.

Since the above mentioned processing is realized by sequentially executing the respective programs simply, a description thereof with reference to flowcharts is omitted.

In the embodiment described hereinbefore, the laser beam is used as the light beam to scan the test surface of the disk. In this case, it is preferable to use S polarized laser beam as the laser beam. In the present invention, however, the light beam is not limited to laser beam and white light beam may be used instead thereof.

Further, although the present invention has been described with reference to the surface defect tester for a disk, the present invention can be used in testing a surface defect of a LCD substrate, etc. Further, although the scanning in the direction R: and the direction θ has been described, the two dimensional XY scanning can be used as a matter of course.

Although, in the embodiment, the recessed defect and the protruded defect are detected similarly, these defects may be detected separately. In the latter case, since deviations of light beams reflected by the recessed defect and the protruded defect in horizontal direction are opposite, it is possible to separately detect the recessed defect and the protruded defect by arranging two parallel rows of light receiving elements in the direction R and determining one of light receiving elements in the two rows, which generates a detection signal first.

What is claimed is:

1. A defect detection optical system for scanning a surface of a flat plate with light beam, receiving a reflection light reflected from the surface by a light receiver and generating a signal for detecting a defect by said light receiver, said defect detection optical system comprising:

a light illuminating system for illuminating said light beam having a width in a direction perpendicular to a main scan direction and relatively scanning said flat plate; and a light receiving system including said light receiver composed of a plurality (n) of light receiving elements, where n is an integer larger than 1, arranged in the direction perpendicular to the main scan direction, for focusing an image of a scan position on said flat plate on said light receiving elements such that the image of the scan position on said flat plate, which is laid in the direction perpendicular to the main scan direction, becomes in the arranging direction of said light receiving elements, wherein, when a width of the image in the main scan direction is equal to or smaller than the width of said light receiving elements and a certain one of said light receiving elements receives a light reflected from a recessed defect or a protruded defect on said surface of said flat plate, the image of the scan position of said flat plate is moved in the width direction of said certain light receiving element, which is perpendicular to the arranging direction of said light receiving elements, and an amount of light received by said certain light receiving element is at least reduced.

2. A defect detection optical system as claimed in claim 1, wherein said flat plate is a disk, the movement of the image in the width direction of said certain light receiving element is caused by light reflected by sloped portions of the recessed or protruded defect and said certain light receiving element of said light receiver generates a signal having two peak values when the recessed or protruded defect is detected by said light receiver.

3. A defect detection optical system as claimed in claim 2, wherein said disk is a substrate, the main scan is a spiral scan and the image of the test point on said flat plate is ellipsoidal having major axis in the arranging direction of said light receiving elements.

4. A defect detection optical system as claimed in claim 3, wherein said substrate is a glass substrate.

5. A surface defect tester including a light receiver, for generating a defect detection signal by scanning a surface of a flat plate with light beam and receiving light beam reflected by said surface of said flat plate, said defect tester comprising:

a light illuminating system for illuminating said light beam having a width in a direction perpendicular to a main scan direction and relatively scanning said flat plate; and a light receiving system including said light receiver composed of a plurality (n) of light receiving elements, where n is an integer larger than 1, arranged in the direction perpendicular to the main scan direction, for focusing an image of a scan position on said flat plate on said light receiving elements such that the image of the scan position on said flat plate, which is laid in the direction perpendicular to the main scan direction, becomes in the arranging direction of said light receiving elements, wherein, when a width of the image in the main scan direction is equal to or smaller than the width of said light receiving elements and a certain one of said light receiving elements receives a light reflected from a recessed defect or a protruded defect on said surface of said flat plate, the image of the scan position of said flat plate is moved in the width direction of said certain light receiving element, which is perpendicular to the arranging direction of said light receiving elements, and an amount of light received by said certain light receiving element is at least reduced.

6. A surface defect tester as claimed in claim 5, wherein said flat plate is a disk, the movement of the image in the width direction of said certain light receiving element is caused by light reflected by sloped portions of the recessed or protruded defect and said certain light receiving element of said light receiver generates a signal having two peak values when the recessed or protruded defect is detected by said light receiver.

7. A surface defect tester as claimed in claim 6, further comprising a detection circuit for generating two detection signals by amplifying the signal having two peak values, wherein said disk is a substrate, the main scan is a spiral scan and the image of the test point on said flat plate is ellipsoidal having major axis in the arranging direction of said light receiving elements.

8. A surface defect tester as claimed in claim 7, wherein said substrate is a glass substrate.

9. A surface defect tester as claimed in claim 8, further comprising a position coordinates generator circuit for generating an information of a scan position of said disk and an A/D converter circuit for converting peak values of the two detection signals into digital values, wherein said defect tester responds to the digital values of the peak values of the two detection signals from said A/D converter circuit and the information of the scan position from said position coordinates generator circuit to obtain a distance between the two detection signals and, when the distance is equal to or smaller than a predetermined value, detects a defect in a position corresponding to a position of said light receiving element.

10. A surface defect tester as claimed in claim 9, further comprising a data processor for calculating an area of the recessed or protruded defect on the basis of the distance between the two detection signals.

11. A surface defect tester as claimed in claim 10, wherein said data processor calculates, as a detection position of the defect, an intermediate position between the scan positions when the two detection signals are generated, determines the continuity thereof to other similar defects on the basis of the intermediate position and a distance between the scan positions and determines the size of defect by grouping continuous defects as one defect.

12. A surface defect tester as claimed in claim 11, wherein said detection circuit comprises n amplifiers for amplifying the n light receiving signals, respectively, and n sample-hold circuits for holding peak values of the detection signals obtained from said n amplifiers, respectively, wherein said A/D converter circuit comprises n A/D converters for A/D converting the peak values held by said sample-hold circuits into digital values.

* * * * *